(12) United States Patent
Wessel

(10) Patent No.: US 8,722,013 B2
(45) Date of Patent: May 13, 2014

(54) USE OF R(+)-ALPHA-LIPOIC ACID FOR CRYPTOGENIC NEUROPATHY

(75) Inventor: Klaus Wessel, Bad Vibel (DE)

(73) Assignee: Encrypta GmbH, Bad Homburg (DE)

( * ) Notice: Subject to any disclaimer, the term of this patent is extended or adjusted under 35 U.S.C. 154(b) by 757 days.

(21) Appl. No.: 12/673,654

(22) PCT Filed: Aug. 14, 2008

(86) PCT No.: PCT/EP2008/060688
§ 371 (c)(1),
(2), (4) Date: Aug. 18, 2010

(87) PCT Pub. No.: WO2009/021991
PCT Pub. Date: Feb. 19, 2009

(65) Prior Publication Data
US 2010/0310538 A1    Dec. 9, 2010

(30) Foreign Application Priority Data

Aug. 16, 2007  (DE) .......................... 10 2007 038 849

(51) Int. Cl.
*A61K 49/00*   (2006.01)
(52) U.S. Cl.
USPC .............................. 424/9.1; 424/436; 424/464
(58) Field of Classification Search
USPC .......................................... 424/9.1, 439, 464
See application file for complete search history.

(56) References Cited

U.S. PATENT DOCUMENTS 6,462,202 B1   10/2002   Schuhbauer et al.
6,900,338 B1   5/2005    Haj-Yehia

FOREIGN PATENT DOCUMENTS

DE    199 38 621 A1    2/2001
WO    WO-00/31060 A1   6/2000
WO    WO-2007/138022 A2   12/2007

OTHER PUBLICATIONS

Maitra et al. "Stereospecific effects of R-lipoic acid on buthionine sulfoximine-induced cataract formation in newborn rats", Biochem. and Biophy. Res. Commu., 1996, 221:422-429.*
Lykkesfeldt et al. "Age-accociated decline in ascorbic acid concentration, recycling, and biosynthesis in rat hepatocytes—reversal with R-alpha-lipoic acid supplementation", FASEB, J. 1998, 12:1183-1189.*
Hagen et al. "(R )-alpha-lipoic acid supplemented old rats have improved mitochondrial function, decreased oxidative damage, and increased metabolic rate", FASEB J., 1999, 13:411-418.*
AIN-93M data sheet, 1 page, 2010.*
Wolfe, M.D. et al., "Chronic Cryptogenic Sensory Polyneuropathy", Archives of Neurology, vol. 56, pp. 540-547 (1999).
Wolfe, M.D. et al., "Cryptogenic Sensory Polyneuropathy", Archives of Neurology, vol. 56, pp. 519-520 (1999).
Ian A. Grant, "Cryptogenic Sensory Polyneuropathy", Peripheral Neuropathy, 4th Edition, vol. 2, Chapter 104, Ed. Dyck, P.J. Thomas, P.K. Elsevier Saunders, Philadelphia, Pennsylvania, U.S.A., pp. 2321-2333 (2005).
Prof. Dr. Schmidt et al., Angew. Chem. International Edit., vol. 4, No. 10, pp. 846-856 (1965).
Ziegler, M.D. et al., Diabetologia, vol. 38, pp. 1425-1433 (1995).
Reljanovic et al., Free Radical Research, vol. 31, No. 3, pp. 171-179 (1999).
Ziegler, M.D. et al., Diabetes Care, vol. 22, No. 8, pp. 1296-1301 (1999).
A. Nassif, "Thioctacid bei der uraemischen Polyneuropathie", Die Medizinische Welt 50/82, pp. 2-4 (1982) (w/English translation of relevant portions).
D. Ziegler et al.; "Effect of antioxidant treatment with alpha-lipoic acid on symptomatic diabetic polyneuropathy: A meta-analysis of four randomized placebo-controlled trials.", Diabetologia, vol. 46, No. Supplement 2, p. A316, (Aug. 2003).
Hahm Jong Ryeal et al.; "Clinical experience with thioctacid (thioctic acid) in the treatment of distal symmetric polyneuropathy in Korean diabetic patients", Journal of Diabetes and Its Complications, vol. 18, No. 2, pp. 79-85 (Mar. 2004).
Liu Fang et al. "Effect of alpha-lipoic acid on the diabetic peripheral neuropathy evaluating by Michigan neuropathy screening instrument", Diabetes, vol. 56, No. Supplement 1, p. A611 (Jun. 2007).
Anonym: "Mit den Nerven am Ende. Polyneuropathien—brennende Schmerzen und Paresen bis hin zu Herzrhythmusstoerungen" Arzte Woche, XP002501721, Retrieved from the Internet: URL:http://www.aerztewoche.at/viewArticleDetails.do?articleID=1262> [retrieved on Oct. 29, 2008], Seite. 1 "Burning Feet" Absatz 2 und 3.

* cited by examiner

*Primary Examiner* — Bin Shen
(74) *Attorney, Agent, or Firm* — Dickstein Shapiro LLP

(57) ABSTRACT

The present invention relates to the use of R(+)-alpha-lipoic acid ((R)-5-(1,2-dithiolan-3-yl)valeric acid) and/or of a physiologically acceptable derivative of this compound for cryptogenic neuropathy.

17 Claims, No Drawings

USE OF R(+)-ALPHA-LIPOIC ACID FOR CRYPTOGENIC NEUROPATHY

The subject matter of the present invention is the use of R(+)-alpha-lipoic acid or a physiologically acceptable derivative of this compound for cryptogenic neuropathy. A further object of the present invention is the use of R(+)-alpha-lipoic acid or a physiologically acceptable derivative of this compound for the production of a presentation form for the treatment of cryptogenic neuropathy.

The presentation form in the sense of the present invention can be developed and marketed as a pharmaceutical composition or medical food. In other words: the invention preferably relates to the use of R(+)-alpha-lipoic acid in the form of a pharmaceutical composition or a medical food for cryptogenic neuropathy.

PRIOR ART

Neuropathies are diseases relating to peripheral nerves and neurons of the sensory, motor and autonomic nervous system. Typically, neuropathies show a progressive loss of function in different areas of the peripheral nervous system. Neuropathies are characterized by a typical clinical disease pattern of symptoms, deficits and clinical features.

"Neuropathies" is not an umbrella term for related disease patterns but a term referring to particular organs for absolutely different diseases with different pathogenesis and pathobiochemistry, different clinical diagnosis and clinical manifestation, different factors of risk, different progression and different prognosis and different therapies. The situation is indeed comparable with different kinds of liver inflammation. There are hepatitis A, B, C only on the basis of different infections, in addition to hereditary, toxic and metabolic hepatids.

Therefore, the most important task of the neurologist is at first the establishment of a differential diagnosis. For that purpose the inspection of the involved nerves (axonopathies, vasculopathies, sensory, motor and autonomic system, symmetric and asymmetric affliction, distal and proximal affliction, affliction of small and large fibers). The affliction of the nerves is associated with the clinical presentation. Motor nerves correlate with muscle weakness and loss of reflex, sensory nerves correlate with the loss of sensory perception as well as positive or negative sensory symptoms. The affliction of autonomic nerves leads to impairment of gastrointestinal functions, bladder weakness, impotence, dysfunctions of sudo and vasomotoric, loss of heart rate variability or clinical symptoms such as angina pectoris. When single nerves are involved, a person skilled in the art uses the term mononeuropathies, in the case that several nerves are involved, the term polyneuropathy is used. Besides the clinical diagnosis chemical laboratory tests, immunological tests, electromyographic examinations and nerve biopsies can be used for the purposes of diagnosis and progression control.

At first, neuropathies may be classified into primary and acquired neuropathies. Into the first group can be classified e.g. the hereditary and inherited neuropathies as well as the idiopathic and also the cryptogenic neuropathy and the autoimmune neuropathies. The acquired neuropathies comprise e.g. the metabolic neuropathies, the toxic neuropathies and the infectious neuropathies. The acquired neuropathies are further distinguished more specifically according to their pathogenic reason: diabetic polyneuropathy, uremic neuropathy, hepatic neuropathy, neuropathies due to vitamin deficiency, hyperthyroid neuropathy, alcoholic neuropathy, cytostatic-induced neuropathies, medicament-induced neuropathies, infectious neuropathies (HIV, leprosy) etc. Hereditary neuropathies are increasingly more distinguished according to their autosomal locus.

The therapies of the individual diseases take aim at the different metabolic, immunologic, infectious or toxicological reasons of the individual disease. Therefore, there is not only one therapy for all neuropathies, but specific therapies for the different diseases according to the pathogenetic basis of the neuropathy.

The prevention of specific noxae is the ultimate therapy for toxic or drug-induced neuropathies, whereas gene therapy may be of help in the case of hereditary neuropathies. In the case of metabolic neuropathies the best result is promised with a therapy of the reason, for example an optimum fine-tuning of blood sugar for diabetic polyneuropathy. For autoimmune neuropathy immunomodulatory and anti-inflammatory therapies are used. So the decision for a therapy of a neuropathy depends on its reason. Only palliative measures such as alleviation of pain are tried with similar therapies for different neuropathies, such as for example through the administration of analgesics or antidepressants.

However, the conclusion that in the case of neuropathic symptoms and deficits and of a factor of risk or a noxa, the diagnosis of the disease is clear is not allowed: a diabetic may indeed suffer from hereditary or immunologic neuropathy, a patient having a genetically verified risk profile may indeed come down with uremic neuropathy. Therefore, always the clinical diagnosis is the decisive step.

α-lipoic acid (LA) has been proposed and tested as an antioxidant for the therapy of different diseases (diabetic polyneuropathy, liver diseases, migraine, auxiliary agent in a therapy with acetylcholine esterase inhibitors for Alzheimer's disease, overweight, as appetite suppressant, for rosacea, for slowdown of aging, etc.).

The R-enantiomer of alpha-lipoic acid ((R)-5-(1,2-dithiolan-3-yl))valeric acid); R-LA has been proposed for the treatment of type II diabetes and insulin resistance due to a specific enantioselective influence of the insulin-dependant glucose transporters (DE 4343593 A1).

Historically, LA as a racemate (rac-LA) was used for the treatment of paresthesia in connection with diabetic polyneuropathy (Germany, Austria). It is provided in solid oral and liquid parenteral formulations (300-600 mg i.v.; 200-600 mg p.o. post i.v.; or 600 mg p.a. only). Due to the unclear clinical evidence of its efficacy it has become questioned by the payers; therefore the producers tried to find an evidence for it.

However, different monocentre clinical trials have been conducted with inconsistent results. In the nineties scientists hypothesized that oxidative stress would contribute to the progression of diabetic neuropathy. At the same time LA has been characterized as an antioxidant. This ex post rationale encouraged the producer to conduct large pivotal multicentre clinical trials to finally find an evidence for the efficacy thereof and to also get the marketing authorisation for this pharmaceutical product worldwide. In a first short-time pilot study of i.v. treatment the results verified the historic impressions of the efficacy (Ziegler, D., M. Hanefeld, K. J. Ruhnau, H. P. Meissner, M. Lobisch, K. Schutte et al. (1995): Treatment of symptomatic diabetic peripheral neuropathy with the anti-oxidant alpha-lipoic acid. A 3-week multicentre randomized controlled trial (ALADIN Study). Diabetologia 38, 1425-1433).

But this result could not be reproduced in pivotal placebo-controlled double-blind multicentre trials either after short-term use (i.v.) or after long-term use (p.o.). The primary working hypothesis was not verified in both pivotal trials and also for none of the secondary parameters which have been formulated a priori signs for efficacy could be found. (Reichel G., Rett K., Lobisch M., Schuette K., Moller W., Tritschler H. J., Mehnert H., Treatment of diabetic polyneuropathy with the antioxidant thioctic acid (alpha-lipoic acid): a two year multicenter randomized double-blind placebo-controlled trial (ALADIN II). Alpha Lipoic Acid in Diabetic Neuropathy. Free Radic Res. 1999; 31:171-179; Ziegler, D., M. Hanefeld, K. J. Ruhnau, H. Hasche, M. Lobisch, K. Schutte et al. (1999b): Treatment of symptomatic diabetic polyneuropathy with the antioxidant alpha-lipoic acid: a 7-month multicenter randomized controlled trial (ALADIN III Study). ALADIN III Study Group. Alpha-Lipoic Acid in Diabetic Neuropathy. Diabetes Care 22, 1296-1301).

To make things worse, the oral long-term therapy appeared to deteriorate the neuropathic deficits. Since that time the clinical use of rac-LA is questioned for the treatment of paresthesia in connection with diabetic polyneuropathy.

rac-LA has also been proposed for the treatment of uremic neuropathy, but a first clinical trial provided negative results (Nassif A., Med. Welt 50 (1982)). The same experience was made in the case of patients with HIV-associated neuropathy and cytostatic-induced neuropathy (personal communication).

In total, from all of these data a negative rationale for the use of LA for neuropathies results. Efforts in proving the efficacy of LA for neuropathies and for establishing LA as a therapeutic for neuropathy have strongly decreased since that time. For a person skilled in the art, namely for a person who develops new pharmaceutical compositions, there was also no reason to do some experiments on this field of research. Instead, racemic lipoic acid and also the natural form are directly sold to consumers as food supplements as free-radical scavengers without medical advice and without medical indication.

Cryptogenic neuropathy is a disease which is characterized by its clinical signs, symptoms and functional deficits of the sensory and autonomic peripheral nerves as well as a slow to very slow progress. It is limited to higher age. So it can clearly be distinguished from other neuropathies and it is a very widespread disease which counts for ca. 23% of all cases of neuropathy (Wolfe G. I. et al. *Chronic cryptogenic sensory polyneuropathy. Archives of Neurology* 56 (5), 1999, 540-547). Its etiology is still unknown. Therefore it is not clear whether it is a distinctively definable disease (Wolfe; Dyck, P. J. *Cryptogenic Sensory Polyneuropathy.* Arch Neurol. 1999; 56(5):519-520), however today it can undoubtedly be stated that the definition of this syndrome and its use are clinically and prognostically useful and valuable (Grant).

For making a diagnosis, at first it is conducted the exclusion of other neuropathic diseases (Wolfe) in the sense of exclusion criteria. In the following a serial differential diagnosis by means of electromyography, quantitative sensory testing, autonomic testing and optionally biopsies of nerves and skin is made and finally serologic tests are performed (Grant, I. A. *Cryptogenic sensory polyneuropathy. In: Peripheral Neuropathy* 4th Edition, vol. 2, Chapter 104, 2321-2333. Ed. Dyck, P. J., Thomas, P. K. Elsevier Saunders, Philadelphia 2005).

The clinical signs of the disease which are revealed by the differential diagnosis are peripherally starting sensory symptoms with and without pain. Although no motor symptoms or deficits can be noticed, abnormalities of the motor nerves can be shown by electromyography. Laboratory values show signs of axonal degeneration. Small and also large fibers are affected. The progression is slow to very slow and the symptoms are very stable (Wolfe).

Due to its unclear efficacy, in general, rac-LA is no longer part of the catalog of benefits of the statutory health insurance in Germany. The efficacy in controlled clinical trials was negative (Mengel K & Zawinell A. *Vitamine and Neuropathiepräparate. In: Arzneimittelverordnungsreport* 2005, Ed. Schwabe & Paffrath. Springer Verlag 2006 Arznei-telegramm 3/94, p. 26).

Therapies of cryptogenic neuropathy with cortisone, immunoglobulins or plasma exchange have been tried, but these experiments were unsuccessful. Also, there is no knowledge about the involvement of oxidative stress in the onset or clinical course of the disease. Thus, there is a need for an effective agent for patients with cryptogenic neuropathy. An agent is required which can be prescribed by a physician for a patient with cryptogenic neuropathy. This can be done in the form of an agent, but preferably in the form of an agent for medical food, because R(+)-alpha-lipoic acid is a physiologically existing substance which is necessary for the metabolism of a human being, but cannot be produced by himself. In food R(+)-alpha-lipoic acid is only present in trace amounts, often covalently bound to proteins and thus not bioavailable.

Furthermore, there is a demand for presentation forms for a support with cryptogenic neuropathy in the sense of medical food. In the sense of the present invention, medical food means food which has been prepared for enteral ingestion or administration under the control of a physician and which is for the specific dietetic support with a disease or with a condition for which characteristic nutrition requirements based on accepted scientific principles by medical evaluation are established (see section 5 (b) Orphan Drug Act (21 U.S.C. 360ee (b) (3)). When in the text below the treatment of cryptogenic neuropathy is mentioned then this on the one hand relates to the medical treatment of the disease, i.e. with pharmaceutical compositions, and on the other hand also preferably to the help for a patient suffering from such a disease by means of medical food.

These objects are solved by the subject matter of the patent claims.

Now it has surprisingly been found that R(+)-alpha lipoic acid ((R)-5-(1,2-dithiolan-3-yl)valeric acid) and/or a physiologically acceptable derivative of this compound are excellently suitable for the treatment and support in the case of cryptogenic neuropathy.

Surprisingly, for the physician this results in the possibility to provide an efficient agent for a patient with cryptogenic neuropathy which has only little adverse effects and good compatibleness. In particular, the agent improves sensory and autonomic deficits which are attributable to cryptogenic neuropathy.

The fatty dithiol acid, alpha-lipoic acid (thioctic acid; 5-(1, 2-dithiolan-3-yl)valeric acid; LA), is widely known and commercially available. This acid in oxidized or reduced form is a cofactor of pyruvate dehydrogenase and an effective antioxidant. Its properties are determined by the dithiolan ring and its high redox potential.

Besides the free acid ((R)-5-(1,2-dithiolan-3-yl)valeric acid) also physiologically acceptable derivatives of this compound can be used. The reduced form of the acid comprising to thiol groups belongs to them. Accordingly, the dithiolans may be administered in oxidized or reduced form. Natural dithiolan acids in nature also exist as dihydro dithiolan acids. Different dehydrogenases and oxidoreductases lead to a biological equilibrium with pools of NADH/NADPH. Through the use of organic groups for the reduction of sulphur instead of hydrogen the metabolism of the dithiolans (in particular the methylation in blood cells, but also the formation of sulfoxides) can be influenced. Therefore methylation is not preferable, because this is an important biological step of elimination. It is rather an aim to delay the early elimination through methylation or oxidation till the target structures are reached, however the biochemical elimination of the reduced groups in the target tissue for forming a pharmacodynamically active dithiolan has still to be possible. For that purpose e.g. thioesters may be used.

Besides the reduced form of R(+)-alpha-lipoic acid as the physiologically acceptable derivatives also the metabolites of this acid as well as chemical modifications of R(+)-alpha-lipoic acid which can be used therapeutically can be mentioned. In such a case e.g. the carboxyl group can be derivatized. Into this class of derivatives inter alia the esters, salts and amides of R(+)-alpha-lipoic acid and R-dihydro lipoic acid can be grouped. As physiologically acceptable salts according to the present invention in particular the sodium, potassium, ammonium, magnesium and calcium salts of the above mentioned compounds are intended. Derivatives are in particular such C1- to C6-alkyl esters of R(+)-alpha-lipoic acid and R-dihydro lipoic acid wherein the carboxyl group has been esterified with a corresponding alcohol. Such R(+)-alpha lipoic acid alkyl esters and R-dihydro lipoic acid esters are for example the methyl ester, ethyl ester, n-propyl ester, isopropyl ester, n-butyl ester, isobutyl ester and tert-butyl ester of R(+)-alpha-lipoic acid and dihydro lipoic acid. Furthermore, also derivatives can be used, the carbon chain of which is changed by shortening, lengthening or incorporation of functional groups. Such changes are for example the incorporation of a carbonyl or ether group into the carbon chain as well as further modifications which are described in Schmidt et al. "Chemistry and Biochemistry of alpha-Lipoic Acid". Angew. Chem. Internat. Edit. Vol. 4 (1965) No. 10.

All of these modifications do not result in a loss of the pharmacodynamic properties. These derivatives comprise structures of the formulae (1), (2) or (3)

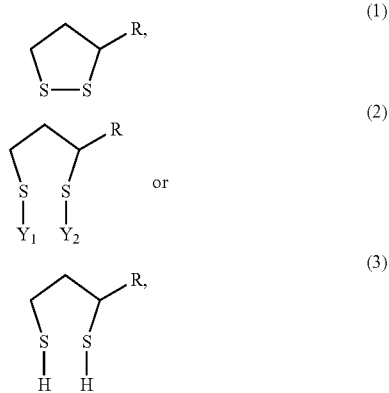

wherein R is an aliphatic or cyclic group having at least 3 carbon atoms which comprises at least one carboxylic acid, carboxylic acid ester or carboxylic acid amide group. Group R preferably comprises 5 to 20 carbon atoms. A preferable group R is in particular the valeric acid group. The groups Y1 and Y2 independently represent a group having 1 to 30 carbon atoms which together with the sulphur atom form a thioester or thioether structure or they represent a metal atom wherein the groups Y1 and Y2 can also form a ring. Y1 and Y2 may also be acetyl or succinyl groups. The resorption and distribution behaviour as well as the metabolism behaviour in the liver (β-oxidation at a carboxylic acid group) may be changed by derivatives. The prevention of early β-oxidation in the case of a carboxylic acid chain results in a better availability of dithiolan acids in the target tissue. Higher lipophilicity of the molecule may lead to an accumulation in nerve tissue. When at group R additional functional groups are attached (as in the case of a carboxylic acid group at the mentioned natural dithiolanes or of an amino group), through this functional group besides the pharmacokinetic profile also the pharmacodynamic profile of the active compound can be changed or amended. So e.g. through the esterification of the dithiolan acids with glycerine the coupling with other pharmacodynamically active substances, also esterified to the glycerine, has been proposed. The aim of this strategy is the formation of a prodrug consisting of two or more active compounds which are covalently attached to each other. The above mentioned derivatives are generally known.

An important commonality of all of these chemical strategies of derivatization is the availability of an intact dithiolan structure in the desired target tissue through the variation of the groups R, Y1 and Y2. However, the metabolism and the pharmacokinetic and the distribution in the organs are influenced. From now on, all these modifications with pharmacodynamically intact dithiolan structure which optionally may also be present in reduced form are summarized under the abbreviation "LA". Differences of the amount of the dose can easily be calculated through cross calculation of the molecular masses in relation to the original R(+)-lipoic acid.

Free and pharmaceutical and chemical conjugates over bridges and spacers with other pharmacodynamically active substances can also be used as combination preparations or prodrugs. The reasons are pharmaceutical, pharmacokinetic and pharmacodynamic improvements which can surprisingly be achieved.

Preferable substances which may be used in combination with R(+)-alpha-lipoic acid ((R)-5-(1,2-dithiolan-3-yl)valeric acid) or a physiologically acceptable derivative of this compound are inter alia vitamins, provitamins, mineral supplements, trace elements, fatty acids, ubiquinone, salicylic acid and physiologically acceptable derivatives of this compound, non-steroidal antiphlogistics, L-carnitine and physiologically acceptable derivatives of this compound, taurine, inositols, choline, N-acetyl cysteine and physiologically acceptable derivatives of this compound, glycerine, hypericum extracts and/or garlic extracts. Examples of preferable vitamins and provitamins are inter alia the vitamins of the B series, in particular thiamine, riboflavin, niacin, pantothenic acid, vitamin C, tocopherols, for example vitamin E, vitamin H (biotin), vitamin A and/or carotenoids, for example β-carotene. Examples of known mineral supplements and trace elements are zinc, magnesium and/or selenium. Preferable fatty acids are in particular unsaturated fatty acids, such as for example γ-linolenic acid and essential fatty acids of the n-3 and n-6 series and derivatives of these compounds, in particular their salts and esters.

The agent according to the present invention for cryptogenic neuropathy may be used in any common administration form. These are inter alia powders, capsules, tablets, solutions, emulsions and suspensions. Capsules and tablets are preferable according to the present invention. Capsules are most preferable, because for this presentation form it has to be noted that R(+)-alpha-lipoic acid can be formulated into tablets only in a laborious way and can polymerize in concentrated solution very easily due to its low melting point.

The agents preferably contain 10 to 300 mg of R(+)-alpha-lipoic acid ((R)-5-(1,2-dithiolan-3-yl)valeric acid) or a physiologically acceptable derivative of this compound. Preferable are 30 to 210 mg of R(+)-alpha-lipoic acid, most preferable are 40 to 160 mg. These amounts relate to single doses.

EXAMPLES

The following cases of patients with an age of between 48 and 78 years and a disease time in the range of 6 months to 5 years surprisingly show the efficacy of R(+)-lipoic acid in the treatment of cryptogenic neuropathy.

Example 1

A patient with cryptogenic neuropathy was treated with an agent according to the present invention. For that purpose a daily oral dose of 50 mg of R-LA (s.d.) was given over a time period of 8 weeks in a customary multivitamin presentation form. The disease is presented by a loss of sensory perception in the feet and a severe impairment of perspiration. Both functions were moderately improved after 8 weeks.

Example 2

A patient with cryptogenic neuropathy was treated with an agent according to the present invention. For that purpose a daily oral dose of 50 mg of R-LA (s.d.) was given over a time period of 12 weeks. The feeling of burning and tingling in the feet and hands has been improved moderately during this time. After the termination of the treatment the symptoms became worse again.

Example 3

A patient with cryptogenic neuropathy was treated with an agent according to the present invention. For that purpose 50 mg of R-LA (s.d.) in an oral multivitamin preparation together with γ-linolenic acid was given. The administration was at first 2 times a day for 6 weeks and then 1 time a day. The lost sensation in the tips of the fingers and toes (Semmes Weinstein monofilament) recovered after 4 weeks. This function improvement was not influenced by a halving of the dose.

Example 4

A patient with cryptogenic neuropathy was treated with an agent according to the present invention. For that purpose a daily oral dose of 100 mg of R-LA as Na salt was given over a time period of 8 weeks. The incontinence and also the control over the bladder were improved after 3 weeks. After 5 weeks the chronic obstipation was no longer a problem: stool is now 5 times a week instead of 2 to 3 times a week to date.

Example 5

A patient with cryptogenic neuropathy was treated with an agent according to the present invention. For that purpose at first a dose of 300 mg of R-LA (Na salt) was given 1 time a day over a time period of 2 weeks and then a dose of 100 mg was given 1 time a day over a time period of 6 weeks. Due to inconsequent taking of the dose on average the agent was only administered every second day. The dryness of the eyes has not changed during the first 3 weeks, but after 4 weeks the use of eye drops was reduced. The feeling of burning in the feet was reduced after 3 weeks (from severe to moderate) and was then unchanged during the following weeks.

Example 6

A patient with cryptogenic neuropathy was treated with an agent according to the present invention. For that purpose at first a daily oral dose of 100 mg of R-LA was given over a time period of one week and then a reduction to a dose of 50 mg for 6 weeks with continuous co-medication of gabapentin followed. The neurological pain in the feet was unchanged, but a pain stimulus with a needle at the feet was not perceived at first and after 3 weeks the pain was perceived moderately, the sensory function was then achieved for a longer time.

Example 7

A patient with cryptogenic neuropathy was treated with an agent according to the present invention. For that purpose at first a daily oral dose of 100 mg of R-LA was given over a time period of two weeks. Then a reduction to a dose of 50 mg followed which was continued over 3 weeks. Subsequently the treatment was continued with the administration of 25 mg over further 3 weeks. The feeling of burning in the feet was improved from severe to moderate after 3 weeks and disappeared completely after 5 weeks. Sharp pain which occurred occasionally was unchanged.

Example 8

A patient with cryptogenic neuropathy was treated with an agent according to the present invention. For that purpose at first a daily oral dose of 100 mg of R-LA was given over a time period of four weeks. Then an anti-oxidative multivitamin preparation together with 50 mg of R-LA was given over 4 weeks. The feeling of burning in the feet was improved from severe to moderate after 2 weeks, but became worse again after 6 weeks.

Example 9

A patient with cryptogenic neuropathy was treated with an agent according to the present invention. For that purpose at first a daily oral dose of 50 mg of R-LA was given over a time period of six weeks. Then an anti-oxidative multivitamin preparation without R-LA was given orally over 4 weeks. The patient suffered from numbness and the loss of sensory perception in the lower limbs. Due to a possible immunologic background ibuprofen was given as a long-term medication. The sensory perception was improved from severe to moderate after 3 weeks and was then stable, the numbness was unchanged. The heart pains during stair climbing disappeared. 3 weeks after the termination of the administration of R-LA the sensory perception became worse again.

Example 10

A patient with cryptogenic neuropathy was treated with an agent according to the present invention. For that purpose a daily dose of 300 mg of R-LA was given over a time period of four weeks together with a continued administration of a vitamin B-combination medication. After 2 weeks a pain stimulus at the feet by means of a sharp needle was perceived again. Stomach pain and feeling of abdominal fullness were improved at the end of that period.

Example 11

A patient with cryptogenic neuropathy was treated with an agent according to the present invention. For that purpose a daily oral dose of 400 mg of R-LA (K salt) was given over a time period of one week. The hyperhidrosis at the face has not disappeared, but the sensory perception in the lower limbs was improved from severe to moderate. 3 months later a formulation of 100 mg (Na salt) was given. The feeling of hyperhidrosis was improved.

Example 12

A patient with cryptogenic neuropathy was treated with an agent according to the present invention. For that purpose a dose of 100 mg of R-LA was given twice a day over a time period of four weeks. The dryness at the feet was improved after 2 weeks, the one at the hands after 3 weeks. The use of moisturizing cream was reduced from 6 to 8 applications to 1 to 2 applications.

The invention claimed is:

1. A method of treating cryptogenic neuropathy which comprises administering to a human subject in need of said treatment, R(+)-alpha-lipoic acid ((R)-5-(1,2-dithiolan-3-yl) valeric acid) or a physiologically acceptable derivative of this compound.

2. The method according to claim 1, characterized in that a physiologically acceptable salt of R(+)-alpha-lipoic acid ((R)-5-(1,2-dithiolan-3-yl)valeric acid) is used.

3. The method according to claim 1, characterized in that R(+)-alpha-lipoic acid ((R)-5-(1,2-dithiolan-3-yl)valeric acid) or a physiologically acceptable derivative of this compound is used in combination with one or more substances selected from the group consisting of vitamins, provitamins, mineral supplements, trace elements, fatty acids, ubiquinone, salicylic acid and physiologically acceptable derivatives of this compound, non-steroidal antiphlogistics, L-carnitine and physiologically acceptable derivatives of this compound, taurine, inositols, choline, N-acetyl cysteine and physiologically acceptable derivatives of this compound, glycerine, hypericum extracts and garlic extracts.

4. The method according to claim 3, characterized in that the vitamins of the B series, are used in the combination.

5. The method according to claim 4, characterized in that zinc, magnesium and/or selenium are used in the combination.

6. The method according to claim 3, characterized in that unsaturated fatty acids and/or physiologically acceptable derivatives of this compounds are used in the combination.

7. A method according to claim 1 in which the R(+)-alpha-lipoic acid ((R)-5-(1,2-dithiolan-3-yl)valeric acid) or a physiologically acceptable derivative of this compound is administered in combination with a carrier.

8. The method according to claim 7, characterized in that the administration form is a capsule.

9. The method according to claim 7, characterized in that the administration form is a tablet.

10. The method according to claim 7, characterized in that the administration form is a solution.

11. The method according to claim 7, characterized in that the administration form is an emulsion.

12. The method according to claim 7, characterized in that the administration form is a suspension.

13. The method according to claim 7, characterized in that the administration form is a powder.

14. The method according to claim 7, characterized in that the administration form contains 10 to 300 mg of R(+)-alpha-lipoic acid ((R)-5-(1,2-dithiolan-3-yl)valeric acid) or a physiologically acceptable derivative of this compound.

15. The method according to claim 3, characterized in that at least one member of the group consisting of thiamine, riboflavin, niacin, pantothenic acid, vitamin C, tocopherols, vitamin H (biotin), vitamin A and carotenoids are used in the combination.

16. The method according to claim 1, characterized in that 10 to 300 mg of R(+)-alpha-lipoic acid ((R)-5-(1,2-dithiolan-3-yl)valeric acid) or a physiologically acceptable derivative of this compound is administered.

17. The method according to claim 16, characterized in that a physiologically acceptable salt of R(+)-alpha-lipoic acid ((R)-5-(1,2-dithiolan-3-yl)valeric acid) is administered.

* * * * *

UNITED STATES PATENT AND TRADEMARK OFFICE
CERTIFICATE OF CORRECTION

PATENT NO. : 8,722,013 B2  Page 1 of 1
APPLICATION NO. : 12/673654
DATED : May 13, 2014
INVENTOR(S) : Klaus Wessel It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 942 days.

Signed and Sealed this
Twenty-ninth Day of September, 2015

Michelle K. Lee
*Director of the United States Patent and Trademark Office*